(12) United States Patent
Lee et al.

(10) Patent No.: US 9,744,167 B2
(45) Date of Patent: Aug. 29, 2017

(54) NANOPARTICULATE COMPOSITIONS AND FORMULATIONS OF PIPERAZINE COMPOUNDS

(71) Applicant: REXAHN PHARMACEUTICALS, INC.

(72) Inventors: Young B. Lee, Clarksburg, MD (US); Chang-Ho Ahn, Potomac, MD (US); Deog J. Kim, Rockville, MD (US)

(73) Assignee: Rexahn Pharmaceuticals, Inc., Rockville, MD (US)

( * ) Notice: Subject to any disclaimer, the term of this patent is extended or adjusted under 35 U.S.C. 154(b) by 262 days.

(21) Appl. No.: 14/317,918

(22) Filed: Jun. 27, 2014

(65) Prior Publication Data
US 2015/0004234 A1    Jan. 1, 2015

Related U.S. Application Data

(60) Provisional application No. 61/840,800, filed on Jun. 28, 2013.

(51) Int. Cl.
*A61K 9/14* (2006.01)
*A61K 31/498* (2006.01)
*A61K 9/51* (2006.01)

(52) U.S. Cl.
CPC ............ *A61K 31/498* (2013.01); *A61K 9/145* (2013.01); *A61K 9/146* (2013.01); *A61K 9/14* (2013.01); *A61K 9/141* (2013.01); *A61K 9/51* (2013.01)

(58) Field of Classification Search
None
See application file for complete search history.

(56) References Cited

U.S. PATENT DOCUMENTS

| | | | |
|---|---|---|---|
| 5,510,118 A | 4/1996 | Bosch et al. | |
| 5,518,187 A | 5/1996 | Bruno et al. | |
| 5,718,388 A | 2/1998 | Czekai et al. | |
| 5,862,999 A | 1/1999 | Czekai et al. | |
| 8,314,100 B2 | 11/2012 | Gong et al. | |
| 8,598,173 B2 | 12/2013 | Gong et al. | |
| 2008/0318963 A1 | 12/2008 | Gong et al. | |
| 2009/0035366 A1 | 2/2009 | Liversidge et al. | |
| 2011/0287065 A1 | 11/2011 | Neville et al. | |

FOREIGN PATENT DOCUMENTS

| | | |
|---|---|---|
| JP | 2008/520653 A | 6/2008 |
| WO | WO-00/52001 A1 | 9/2000 |
| WO | WO-2006/054830 | 5/2006 |

OTHER PUBLICATIONS

Lee et al., "Synthesis, anticancer activity and pharmacokinetic analysis of 1-[(substituted 2-alkoxyquinoxalin-3-yl)aminocarbonyl]-4-(hetero)arylpiperazine derivatives" Bioorganic & Medicinal Chemistry 20 (2012) 1303-1309.
Wu et al., "Physical and chemical stability of drug nanoparticles," Advanced Drug Delivery Reviews, vol. 66, 2011, p. 456-469.
Nowosielski, R et al., "Structure and Properties of Barium Ferrite Powders Prepared by Milling and Annealing," Archives of Materials Science and Engineering, vol. 28, No. 12, Dec. 2007, pp. 735-742 [online], [retrieved on Sep. 4, 2014], Retrieved from the Internet <URL:http://www.w.archivesmse.org/vol28_12/28125.pdf>.
Ren, R et al., "Polymorphic Transformation and Powder Characteristics of Tio2 During High Energy Milling," Journal of Materials Science, vol. 35, 2000, pp. 6015-6026 [online], [retrieved on Sep. 4, 2014], Retrieved from the Internet <URL:http://www.crystallography.ru/MA/articles/TiO2-temperature-2000.pdf>.
International Search Report and Written Opinion in PCT/US14/44714, dated Oct. 16, 2014.
Merisko-Liversidge et al., "Nanosizing for oral and parenteral drug delivery: A perspective on formulating poorly-water soluble compounds using wet media milling technology," Advanced Drug Delivery Reviews, vol. 63, pp. 427-440 (2011).

*Primary Examiner* — James Rogers
(74) *Attorney, Agent, or Firm* — Keith G. Haddaway; Annette K. Kwok

(57) ABSTRACT

The present invention relates to storage stable nanoparticulate compositions of piperazine compounds. The pharmaceutical compositions comprising the nanoparticulate compositions that are useful for the treatment and prevention of proliferative diseases including cancer are also described.

19 Claims, 4 Drawing Sheets

NANOPARTICULATE COMPOSITIONS AND FORMULATIONS OF PIPERAZINE COMPOUNDS

FIELD OF THE INVENTION

Figure 1:
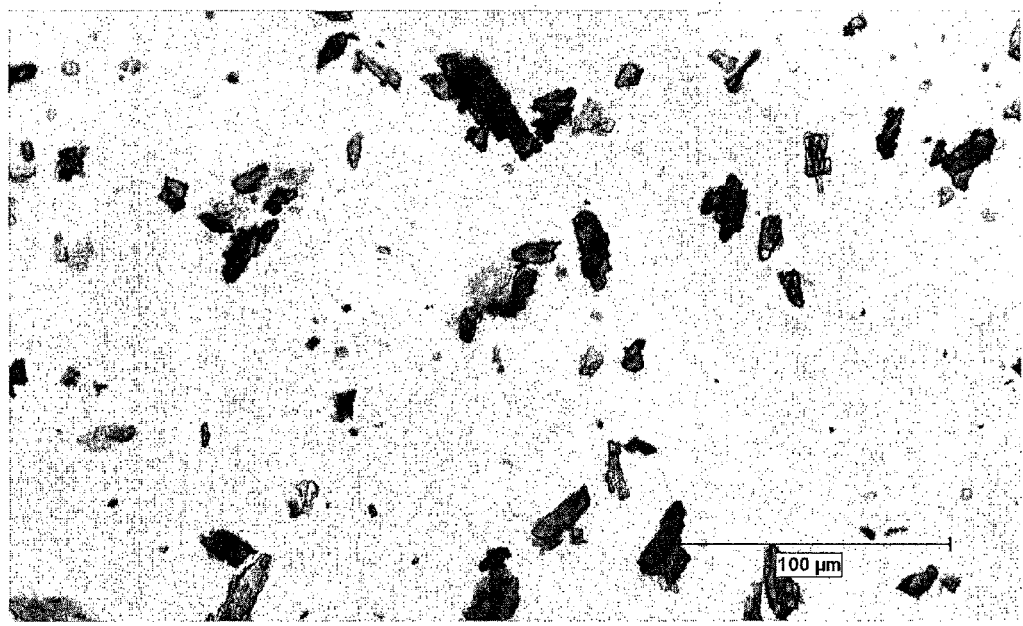

The present invention relates to nanoparticulate compositions in which the active agent is a piperazine compound and pharmaceutical compositions including the nanoparticulate compositions. More particularly, the invention is a nanoparticulate composition that includes 1-(3,5-dimethoxyphenyl)-4-[(6-fluoro-2-methoxyquinoxalin-3-yl)aminocarbonyl]piperazine. The compositions and formulations are useful for the treatment and prevention of proliferative diseases including cancer.

BACKGROUND OF THE INVENTION 1-(3,5-Dimethoxyphenyl)-4-[(6-fluoro-2-methoxyquinoxalin-3-yl)aminocarbonyl]piperazine and related compounds and derivatives are described in U.S. Pat. No. 8,314,100, incorporated herein by reference in its entirety. Such compounds have been shown to have significant anti-tumor activity, but have very poor solubility in water.

Methods of making nanoparticulate compositions are described, for example, in U.S. Pat. Nos. 5,518,187 and 5,862,999, both for "Method of Grinding Pharmaceutical Substances"; U.S. Pat. No. 5,718,388; for "Continuous Method of Grinding Pharmaceutical Substances"; and U.S. Pat. No. 5,510,118 for "Process of Preparing Therapeutic Compositions Containing Nanoparticles".

SUMMARY OF THE INVENTION

The present invention relates to nanoparticulate compositions of piperazine compounds such as 1-(3,5-dimethoxyphenyl)-4-[(6-fluoro-2-methoxyquinoxalin-3-yl)aminocarbonyl]piperazine or related compounds and derivatives as described elsewhere herein, as the active agent, and at least one surface stabilizer.

The present invention also relates to methods of making the nanoparticulate compositions of the present invention. Such methods include reducing the size of particles of a piperazine compound for a time and under conditions sufficient to provide a nanoparticulate composition and contacting the compound with at least one surface stabilizer. The one or more surface stabilizers can be contacted with the piperazine either before, during, or after size reduction of piperazine particles.

The present invention also relates to pharmaceutical compositions of the nanoparticulate compositions of the present invention and a pharmaceutically acceptable carrier, as well as any pharmaceutical acceptable excipients.

The present invention also relates to methods of treatment using the pharmaceutical compositions of the present invention for conditions, such as proliferative diseases or diseases that are associated with or triggered by persistent angiogenesis.

In particular embodiments, the invention is a stable composition that includes:

(a) nanoparticles of compound of formula (1),

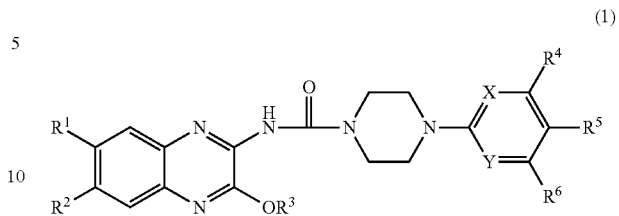

(1)

or pharmaceutically acceptable salts thereof,
wherein
X and Y are independently N or C—R$^7$;
for the combination of variables R$^1$ and R$^2$:
 R$^1$ is hydrogen, C$_1$-C$_3$ alkoxy, C$_1$-C$_3$ alkyl or halogen and R$^2$ is F; or
 R$^1$ is F and R$^2$ is hydrogen, C$_1$-C$_3$ alkoxy, C$_1$-C$_3$ alkyl or halogen;
R$^3$ is C$_1$-C$_3$ alkyl; and
R$^4$, R$^5$, R$^6$ and R$^7$ are independently H, C$_1$-C$_6$ alkoxy, C$_1$-C$_6$ alkyl, C$_1$-C$_6$ haloalkyl, C$_1$-C$_6$ alkylcarbonyl, cyano, nitro or halogen; and (b) at least one surface stabilizer, wherein the nanoparticles have an effective median particle size (D50) of less than about 1,000 nm. The compound of formula (1) can be 1-(3,5-dimethoxyphenyl)-4-[(6-fluoro-2-methoxyquinoxalin-3-yl)aminocarbonyl]piperazine. The at least one surface stabilizer can be at least one polyalkylene oxide such as a block copolymer of polyethylene oxide and polypropylene oxide. In some embodiments, the at least one surface stabilizer is a poloxamer, such as poloxamer 407 or poloxamer 338. In some embodiments, the composition is in the form of a liquid suspension. In other embodiments, the composition is in the form of a dry solid. In some embodiments, the composition is stable after storage for at least four weeks. In other embodiments, particularly those in the form of a powder, the composition is stable after storage for at least 6 months. In some embodiments, the effective median particle size is less than about 500 nm. The ratio (wt/wt) of the compound of formula (1) to surface stabilizer in the composition can be from about 100:1 to about 5:1.

In another aspect, the invention is a method of making a composition as recited above by preparing a mixture of particles of a compound of formula (1), or pharmaceutically acceptable salts thereof, for example, 1-(3,5-dimethoxyphenyl)-4-[(6-fluoro-2-methoxyquinoxalin-3-yl)aminocarbonyl]piperazine, and (b) at least one surface stabilizer, and reducing the size of the particles of a compound of formula (1) under conditions sufficient to provide a nanoparticulate suspension having an effective median particle size of less than about 1,000 nm, to form a stable composition. The method can further include the step of drying the nanoparticulate suspension, for example by lyophilizing a frozen suspension, to form a powder. The method can also include water in the mixture. The mixture can include from about 5% to about 50% of the compound of formula (1) and from about 0.1% to about 5% of the surface stabilizer or, typically in solid forms, from about 75% to about 90% of the compound formula (1) and from about 10% to about 25% of the surface stabilizer. The ratio of the compound of formula (1) to surface stabilizer can be from about 100:1 to about 5:1. Reducing the size of particles can be accomplished by milling, homogenizing or precipitation, for example by wet milling. The milling can be any amount of time suitable to provide the desired size, for example, for about 600 minutes or about 360 minutes or any time period in between. The suspension can be diluted with a solvent such as water after reducing the size of the particles. A poloxamer solution can also be added to the mixture after reducing the size of the particles.

In another aspect, the invention is a pharmaceutical composition that includes the nanoparticle composition as described above and at least one pharmaceutically acceptable excipient. The at least one pharmaceutically acceptable excipient can be, for example, water or hydroxypropyl methylcellulose. The composition can be in an oral dosage form or a parenteral dosage form, and can include, for example, from about 0.01 to about 250 mg of the compound of formula (1), and can include, for example from about 0.001% to about 99.5% of the compound of formula (1).

The invention also includes a method of treating a tumor by administering to an animal in need thereof a composition or pharmaceutical composition as described above.

Further objectives and advantages, as well as the structure and function of preferred embodiments will become apparent from a consideration of the description, drawings, and examples.

DETAILED DESCRIPTION OF THE DRAWINGS

FIG. 1: 1-(3,5-Dimethoxyphenyl)-4-[(6-fluoro-2-methoxyquinoxalin-3-yl)aminocarbonyl]piperazine at 400× Magnification.

Figure 2:
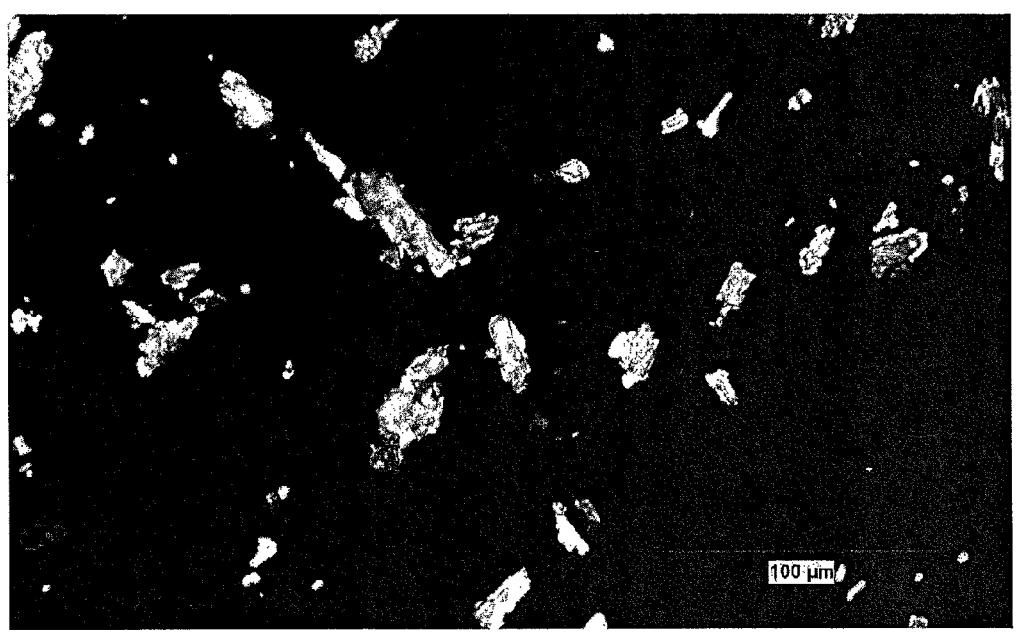

FIG. 2: 1-(3,5-Dimethoxyphenyl)-4-[(6-fluoro-2-methoxyquinoxalin-3-yl)aminocarbonyl]piperazine at 400× magnification, polarized light.

Figure 3:
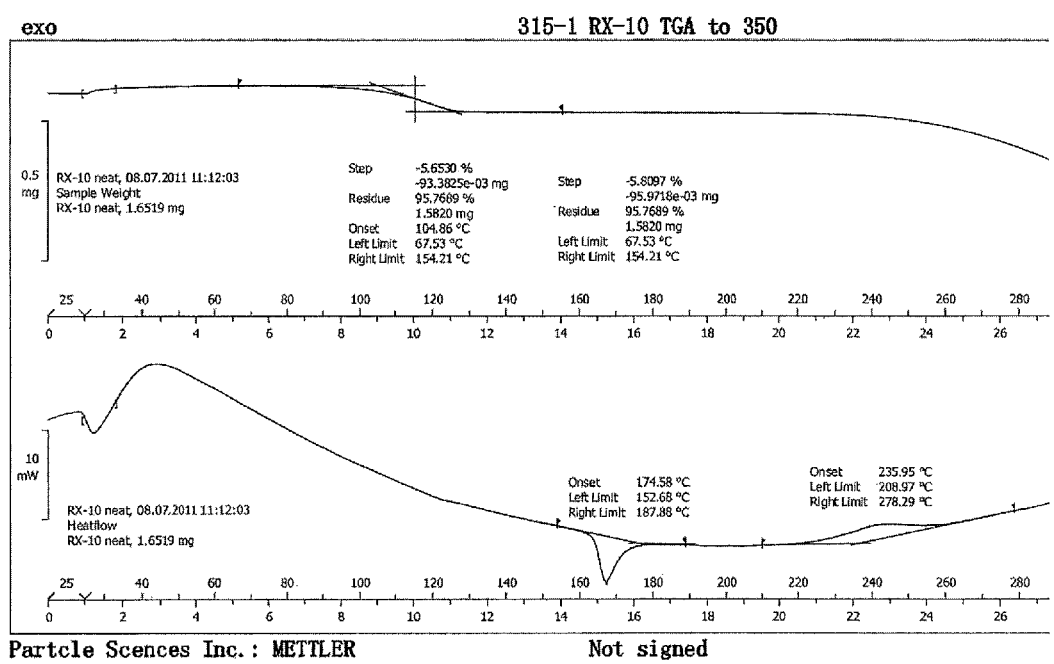

FIG. 3: Thermogravimetric analysis of 1-(3,5-dimethoxyphenyl)-4-[(6-fluoro-2-methoxyquinoxalin-3-yl)aminocarbonyl]piperazine.

Figure 4:
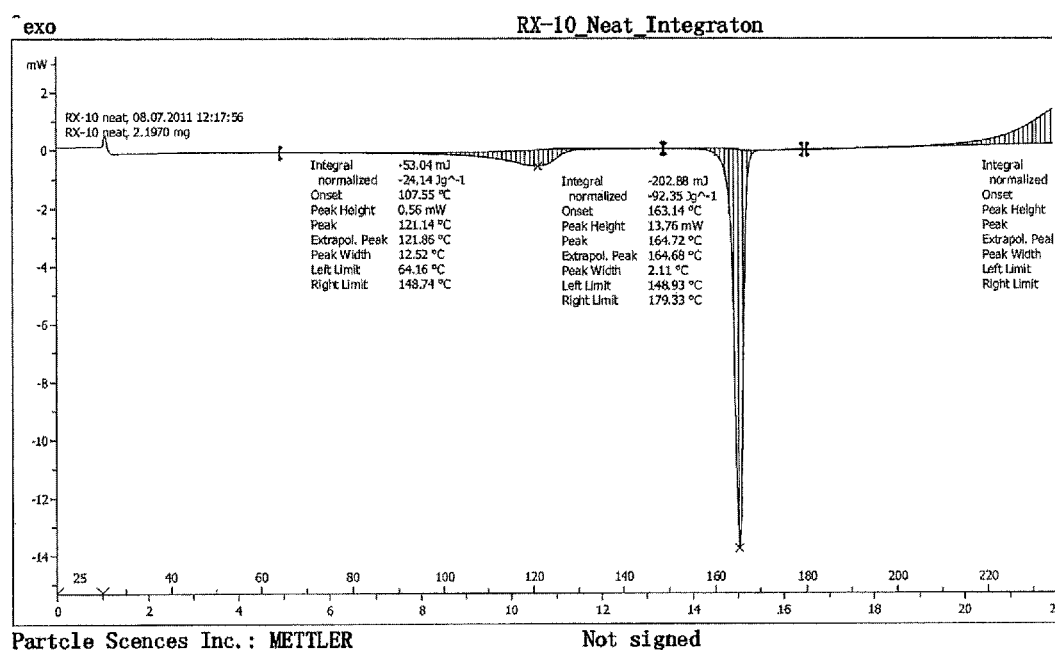

FIG. 4: Differential Scanning calorimetry Thermograph of 1-(3,5-dimethoxyphenyl)-4-[(6-fluoro-2-methoxyquinoxalin-3-yl)aminocarbonyl]piperazine.

DETAILED DESCRIPTION OF THE INVENTION

Embodiments of the invention are discussed in detail below. In describing the embodiments, specific terminology is employed for the sake of clarity. However, the invention is not intended to be limited to the specific terminology so selected. While specific exemplary embodiments are discussed, it should be understood that this is done for illustration purposes only. A person skilled in the relevant art will recognize that other components and configurations can be used without parting from the spirit and scope of the invention. All references cited herein are incorporated by reference as if each had been individually incorporated.

Piperazine compounds of formula (1),

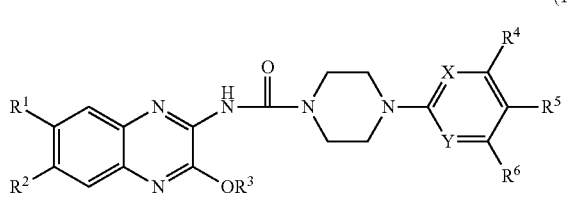

(1)

wherein
X and Y are independently N or C—$R^7$;
for the combination of variables $R^1$ and $R^2$:
$R^1$ is hydrogen, $C_1$-$C_3$ alkoxy, $C_1$-$C_3$ alkyl or halogen and $R^2$ is F; or
$R^1$ is F and $R^2$ is hydrogen, $C_1$-$C_3$ alkoxy, $C_1$-$C_3$ alkyl or halogen;
$R^3$ is $C_1$-$C_3$ alkyl; and
$R^4$, $R^5$, $R^6$ and $R^7$ are independently H, $C_1$-$C_6$ alkoxy, $C_1$-$C_6$ alkyl, $C_1$-$C_6$ haloalkyl, $C_1$-$C_6$ alkylcarbonyl, cyano, nitro or halogen;
have been shown to be useful for the treatment of hyperproliferative disorders. For example, such compounds can be used for treating tumors, particularly a tumor (or cancer and/or any metastases). Tumors treatable with compounds of formula (1) include a tumor which is a breast cancer, lung cancer, gastrointestinal cancer, including esophageal, gastric, small bowel, large bowel and rectal cancer, glioma, sarcoma, such as those involving bone, cartilage, soft tissue, muscle, blood and lymph vessels, ovarian cancer, myeloma, lymphoma, leukemia, cervical cancer, endometrial cancer, head and neck cancer, mesothelioma, renal cancer, ureter, bladder and urethral cancers, colon cancer, colorectal cancer, liver cancer, pancreatic cancer, prostate cancer, skin cancers and melanoma. Effective treatment with a compound of formula (1) requires a composition that can deliver the compound to the tumor. Compounds of the invention have been tested in vitro against cancer cells lines and have shown activities in the inhibition of cancer cell growth. For example, U.S. Pat. No. 8,314,100 describes that compounds of the invention have shown activity against: Human OVCAR-3 (ovary), MCF-7 (breast, hormone-dependent), MDA-MB-231 (breast), PC3 (prostate), HepG2 (liver), A549 (lung), Caki-1 (kidney), HT-29 (colon), HCT116 (colon) and PANC-1 (pancreas) from the American Type Culture Collection (ATCC) (Manassas, Va.); MKN-45 (stomach) from DSMZ (Germany); UMRC2 (kidney) from the U.S. National Cancer Institute (Bethesda, Md.); Huvec (human umbilical vein endothelial cells), HEK293 (human embryonic kidney) and SK-OV-3 (overy) from Korean Cell Line Bank (Seoul, Korea).

An example of a compound of formula (1) is 1-(3,5-Dimethoxyphenyl)-4-[(6-fluoro-2-methoxyquinoxalin-3-yl) aminocarbonyl]piperazine (Compound A):

Compound A

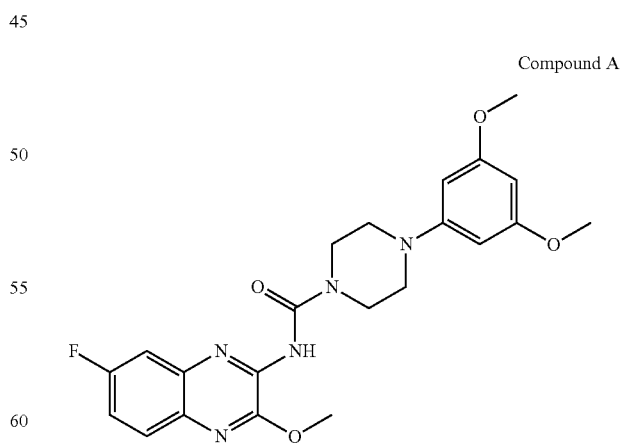

Compound A has very poor solubility in water, less than 0.1 μg/ml. This poor solubility in water makes it difficult to deliver the compound and related compounds of formula (1) and has limited clinical development, thus creating a need for the development of a formulation suitable for clinical use. The present invention was developed with a goal of obtaining a suitable formulation that can provide a stable suspension of the compound at a concentration of about 100 mg/mL or a dried formulation that could be either delivered orally or used to prepare a stable suspension. While the invention is described and exemplified primarily with respect to 1-(3,5-dimethoxyphenyl)-4-[(6-fluoro-2-methoxyquinoxalin-3-yl)aminocarbonyl]piperazine, it is to be understood that the invention is applicable to other compounds of formula (1).

In order to improve bioavailability, the present formulation was developed with the concept of obtaining a submicron particle size distribution of the piperazine compound in a suspension using a minimum of excipients that are generally regarded as safe (GRAS) to reduce potential toxic interference during the study. Test articles of the prototype formulation will be made from a scaled-up process under best-clean conditions. Additionally, the remaining suspension is intended to serve as the basis for future work in developing a solid-dosage formulation of, for example, 1-(3,5-dimethoxyphenyl)-4-[(6-fluoro-2-methoxyquinoxalin-3-yl)aminocarbonyl]piperazine.

"Active agent", "drug", "Active Pharmaceutical Ingredient", or "API" as used herein, refers to compounds of formula (1),

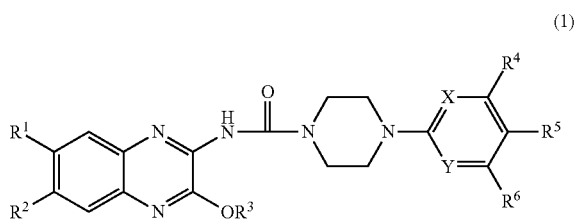

(1)

wherein

X and Y are independently N or C—$R^7$;

for the combination of variables $R^1$ and $R^2$:

$R^1$ is hydrogen, $C_1$-$C_3$ alkoxy, $C_1$-$C_3$ alkyl or halogen and $R^2$ is F; or $R^1$ is F and $R^2$ is hydrogen, $C_1$-$C_3$ alkoxy, $C_1$-$C_3$ alkyl or halogen;

$R^3$ is $C_1$-$C_3$ alkyl; and $R^4$, $R^5$, $R^6$ and $R^7$ are independently H, $C_1$-$C_6$ alkoxy, $C_1$-$C_6$ alkyl, $C_1$-$C_6$ haloalkyl, $C_1$-$C_6$ alkylcarbonyl, cyano, nitro or halogen. Exemplary embodiments of compounds of formula (1) include the following:

| Compound | $R^1$ | $R^2$ | $R^3$ | $R^4$ | $R^5$ | $R^6$ | X | Y |
|---|---|---|---|---|---|---|---|---|
| Compound A | F | H | Me | OMe | H | OMe | C—H | C—H |
| Compound B | F | H | Me | Me | H | Me | C—H | C—H |
| Compound C | F | H | Me | H | H | H | C—OMe | C—H |
| Compound D | F | H | Me | OMe | H | H | C—H | C—H |
| Compound E | F | H | Me | Me | H | H | C—H | C—H |
| Compound F | F | H | Me | Cl | H | H | C—H | C—H |

The active agent can be in a free form, or pharmaceutically acceptable salt form, in the form of their possible enantiomers, diasteromers and relative mixtures, polymorphs, amorphous, partially amorphous forms, solvates (including hydrates), their active metabolites and prodrugs.

"Poorly water soluble", as used herein, has the meaning generally attributable in the art. For example, poorly water soluble can mean having a solubility in water at 20° C. of less than 1%, e.g., 0.01% weigh/volume, i.e., a "sparingly soluble to very slightly soluble drug" as described in Remington: The Science and Practice of Pharmacy, 19th Edition, A. R. Gennaro, Ed., Mack Publishing Company, US, Vol. 1, p. 195 (1995). Other similar generally recognized definitions are encompassed by the term.

By "an effective median particle size of less than about 1,000 nm" it is meant that at least 50% of the nanoparticulate active agent particles have a particle size of less than about 1,000 nm, as determined on the basis of the weight average particle size as measured by conventional particle size measuring techniques well-known to those skilled in the art. Such techniques include light scattering methods, microscopy and other conventional techniques, e.g., sedimentation field flow fractionation, photon correlation spectroscopy, light scattering and disk centrifugation. As will be recognized, similar language related to other effective particle sizes have similar definitions. Mean or average particle size can be determined similarly. Designations of particle sizes and other description of particle size will be recognized by persons skilled in the art. For example, D50, the median, describes a composition with a population of nanoparticulate active agent particles where half of the population has a diameter below this value. Similarly, D90 describes the population where the diameter of ninety percent of the distribution has a smaller particle size and ten percent has a larger particle size. The D10 describes the population where the diameter of ten percent of the particles is smaller than and ninety percent of the particles larger than the stated value.

The terms "effective amount" or "pharmaceutically effective amount" of a nanoparticle formulation or composition, as provided herein, refer to a nontoxic but sufficient amount of the nanoparticle formulation or composition to provide the desired response and corresponding therapeutic effect, in an amount sufficient to effect treatment of the subject. As will be pointed out below, the exact amount required will vary from subject to subject, depending on the species, age, and general condition of the subject, the severity of the condition being treated, mode of administration and the like. An appropriate "effective" amount in any individual case may be determined by one of ordinary skill in the art using routine experimentation.

The phrase "pharmaceutically acceptable" or "pharmacologically acceptable" means a material which is not biologically or otherwise undesirable, i.e., the material may be administered to an individual along with the nanoparticle formulation or composition without causing any undesirable biological effects or interacting in a deleterious manner with any of the components of the composition in which it is contained.

The active pharmaceutical ingredient (API), 1-(3,5-dimethoxyphenyl)-4-[(6-fluoro-2-methoxyquinoxalin-3-yl)aminocarbonyl]piperazine, as well as related compounds described herein, is being investigated as an anti-cancer treatment for solid tumors that has the potential to be well absorbed by the intestine when tested in vitro and that demonstrates good oral bioavailability in animal model studies. Because of the poor aqueous solubility of 1-(3,5-dimethoxyphenyl)-4-[(6-fluoro-2-methoxyquinoxalin-3-yl)aminocarbonyl]piperazine, production of a submicron suspension needed to be developed as a viable oral delivery option to avoid the need to administer large volumes of a 1-(3,5-dimethoxyphenyl)-4-[(6-fluoro-2-methoxyquinoxalin-3-yl)aminocarbonyl]piperazine solution to achieve the intended dosage levels.

In exemplary embodiments, the invention is a formulation that is a stable nanoparticulate composition of a compound of formula (1), for example 1-(3,5-dimethoxyphenyl)-4-[(6-fluoro-2-methoxyquinoxalin-3-yl)aminocarbonyl]piperazine (Compound A) having an effective median particle size (D50) of less than about 1,000 nm and preferably at least one surface stabilizer. The composition can be in the form of a suspension, typically in water, or a dried powder. In exemplary embodiments of the invention in dried form, the nanoparticulate composition can be redispersed such that the effective median particle size of the redispersed compound of formula (1) is less than about 1,000 nm. This is significant in that it allows the nanoparticulate compound to redisperse to a substantially small particle size to provide benefits similar to those of the suspension having a similar nanoparticulate particle size.

In exemplary embodiments, the particles in a suspension, whether as originally prepared, as a redispersed solid, or in a solid form, can have an effective median particle size of less than about 1,000 nm, less than 500 nm, less than about 250 nm, or less than about 100 nm. In exemplary embodiments, the particles in a suspension, whether an originally prepared or as a redispersed solid, or in a solid form can have an effective mean particle size of less than about 1,000 nm, less than 500 nm, less than about 250 nm, or less than about 100 nm. In exemplary embodiments, the median or mean particle size can be, for example, from about 100 nm to about 1,000 nm, from about 100 nm to about 500 nm, from about 200 nm to about 1,000 nm, from about 200 nm to about 500 nm, from about 100 nm to about 200 nm, or from about 250 nm to about 500 nm. In exemplary embodiments, the particles in a suspension, whether as originally prepared, as a redispersed solid, or in a solid form can have an effective median or mean particle size of more than about 100 nm, more than about 250 nm, or more than about 500 nm.

In accordance with the present invention, the active agent may be present in an amount by weight of from about 0.001% to about 99.5%, from about 0.1% to about 95% by the dried weight of the composition or formulation. In some embodiments, the active agent is present in an amount of from about 0.5% to about 90% by the dried weight of the composition or formulation. In some embodiments, the active agent may be present in an amount of from about 5% to about 50%, for example from about 5% to about 40%, from about 10% to about 30%, or from about 10% to about 40%. In some embodiments of the invention that are in the form of a suspension, the active agent may be present in an amount of from about 5% to about 50%, for example from about 5% to about 40%, from about 10% to, about 30%, or from about 10% to about 40%. In other exemplary embodiments, the active agent may be present in an amount of from about 75% to about 99%, for example from about 75% to about 90%, from about 80% to about 99%, or from about 90% to about 99%. In other exemplary embodiments of a dried form of the composition, the active agent may be present in an amount of from about 75% to about 99%, for example from about 75% to about 90%, from about 80% to about 99%, or from about 90% to about 99%. In other exemplary embodiments of a dried form of the composition, the active agent may be present in an amount of about 75%, about 80%, about 90%, about 95%, or about 99%.

Methods of characterizing the API included not only optical methods, but also thermal methods, as all milling processes, including those of relatively low-energy, can generate localized heating at the particulate level. Thermal data can be used to determine if the active agent exhibits any thermal transitions that could be detrimental to particle size reduction under milling stresses.

As the simplest and most practical size reduction method, media milling was chosen to initiate the study. In media milling, the API is mixed with a milling aid, typically a surfactant, and made into slurry with milling media, spherical beads of a hard, inert material. Particles are broken down through mechanical abrasion by agitating the slurry, either by low-energy means, such as rolling it in a container on a roller mill, or by high-energy means, such as mixing it with a rotary agitator, known as a spindle mill.

Several GRAS milling aids were selected for their suitability in oral dosage forms, and were tested for milling efficacy at different concentrations with different levels of API. From these development samples, potential candidates were selected and then monitored for particle-size stability over time. The leading candidate from these was scaled-up and used to process API in bulk for toxicity studies under GLP best-clean conditions.

Other methods of size reduction, such as microfluidization and nucleation or precipitation, were considered as alternatives had media milling proved unsuccessful and can be used in embodiments of the invention. Microfluidization involves forcing a suspension of the API through a narrow aperture under high pressure (up to 25,000 psi) using the shear forces so generated to break apart the particles. To reduce particles in size by precipitation, the API is dissolved in a suitable solvent and then combined with a miscible antisolvent; which destabilizes the solution, and causes the API to precipitate. Variations in the rate of solvent/antisolvent combination as well as the addition of segregating agents and high-energy disruption can produce reduced-size particles.

In the present invention, roller milling was chosen to process the compound of formula (1) (Compound A as an example) because it is an uncomplicated procedure for particle size reduction that not only results in high process yields, even in small test batches, but also poses a minimal likelihood of personnel exposure to highly potent API. Sterile Water for Injection (SWFI) was used instead of purified water to reduce the potential for microbial contamination.

Surface Stabilizer

Surface stabilizers which can be employed in the invention include, but are not limited to, known organic and inorganic pharmaceutical excipients. Such excipients include various polymers, low molecular weight oligomers, natural products and surfactants. Surface stabilizers include nonionic type, cationic type, anionic type, and zwitterionic type surfactants. Examples of nonionic surface stabilizers include ethoxylated aliphatic alcohol, polyoxyethylene surfactants, carboxylic esters, polyethylene glycol esters, anhydrosorbitol ester and its ethoxylated derivatives, glycol esters of fatty acids, carboxylic amides, monoalkanolamine condensates, and polyoxyethylene fatty acid amides. Examples of cationic surface stabilizers include quaternary ammonium salts, amines with amide linkages, polyoxyethylene alkyl and alicyclic amines, N,N,N',N' tetrakis substituted ethylenediamines, and 2-alkyl 1-hydroxyethyl 2-imidazolines. Examples of anionic surface stabilizers include carboxylates, sulphonates, petroleum sulphonates, alkylbenzenesulphonates, naphthalenesulphonates, olefin sulphonates, alkyl sulphates, sulphates, sulphated natural oils and fats, sulphated esters, sulphated alkanolamides and alkylphenols, ethoxylated and sulphated. Examples of zwitterionic surface stabilizers include N-coco 3-aminopropionic acid/sodium salt, N-tallow 3-iminodipropionate, disodium salt, N-carboxymethyl-N-dimethyl-N-9 octadecenyl ammonium hydroxide and N-cocoamidethyl-N-hydroxyethylglycine, sodium salt.

Representative examples of surface stabilizers include poloxamers, which are block copolymers of ethylene oxide and propylene oxide, gelatin, casein, lecithin (phosphatides), dextran, gum acacia, cholesterol, tragacanth, stearic acid, benzalkonium chloride, calcium stearate, glycerol monostearate, cetostearyl alcohol, cetomacrogol emulsifying wax, sorbitan esters, polyoxyethylene alkyl ethers (e.g., macrogol ethers, such as cetomacrogol 1000), polyoxyethylene castor oil derivatives, polyoxyethylene sorbitan fatty acid esters (e.g., the commercially-available Tweens®, such as, e.g., Tween 20® and Tween® (ICI Specialty Chemicals)); polyethylene glycols (e.g., Carbowax 3550® and Carbowax 934® (Union Carbide)), polyoxyethylene stearates, colloidal silicon dioxide, phosphates, carboxymethylcellulose calcium, carboxymethylcellulose sodium, methylcellulose, hydroxyethylcellulose, hydroxypropylmethylcellulose phthalate, noncrystalline cellulose, magnesium aluminium silicate, triethanolamine, polyvinyl alcohol (PVA), 4-(1,1,3,3-tetramethylbutyl)-phenol polymer with ethylene oxide and formaldehyde (also known as tyloxapol, superione and triton); and poloxamines.

Exemplary surface stabilizers include Pluronics®, e.g., Poloxamer 105 (Pluronic® L35), Poloxamer 108 (Pluronic® F38), Poloxamer 124 (Pluronic® L44NF), Poloxamer 184 (Pluronic® L-64), Poloxamer 188 (Pluronic® F68NF), Poloxamer 237 (Pluronic® F87NF), Poloxamer 238 (Pluronic® F88), poloxamer 338 (Pluronic® F108NF), Poloxamer 401 (Pluronic® L121), Poloxamer 407 (Pluronic®F127NF) and other poloxamer products; Tetronics®, e.g., Tetronic 904, 908, 1107, and 90R4, which are tetrafunctional block copolymers derived from sequential addition of propylene oxide and ethylene oxide to ethylenediamine (BASF Wyandotte Corporation, Parsippany, N.J.)); Tetronic 15080 (T-1508) (BASF Wyandotte Corporation), Tritons X-2000, which is an alkyl aryl polyether sulfonate (Rohm and Haas); Crodestas F-100®, which is a mixture of sucrose stearate and sucrose distearate (Croda Inc.); p-isononylphenoxypoly-(glycidol), also known as Olin-10G® or Surfactant 10-Go (Olin Chemicals, Stamford, Conn.); Crodestas SL-400 (Croda, Inc.); and SA9OHCO, which is C18H37CH2(CON(CH3)-CH2(CHOH)4 (CH2OH)2 (Eastman Kodak Co.); decanoyl-N-methylglucamide; n-decyl-beta-D-glucopyranoside; n-decyl-beta-D-maltopyranoside; n-dodecyl-beta-D-glucopyranoside; n-dodecyl-beta-D-maltoside; heptanoyl-N-methylglucamide; n-heptyl-beta-D-glucopyranoside; n-heptyl-beta-D-thioglucoside; n-hexyl-beta-D-glucopyranoside; nonanoyl-N-methylglucamide; n-nonyl-beta-D-glucopyranoside; octanoyl-N-methylglucamide; n-octyl-beta-D-glucopyranoside; octyl-beta-D-thioglucopyranoside; PEG-phospholipid, PEG-cholesterol, PEG-cholesterol derivative, PEG-vitamin A, PEG-vitamin E, lysozyme, random copolymers of vinyl pyrrolidone and vinyl acetate and the like.

Examples of useful cationic surface stabilizers include, but are not limited to, polymers, biopolymers, polysaccharides, cellulosics, alginates, phospholipids, and nonpolymeric compounds, such as zwitterionic stabilizers, poly-n-methylpyridinium, anthryl pyridinium chloride, cationic phospholipids, chitosan, polylysine, polyvinylimidazole, polybrene, polymethylmethacrylate trimethylammonium bromide (PMMTMABr), hexyldesyltrimethylammonium bromide (HDMAB), and polyvinylpyrrolidone-2-dimethylaminoethyl methacrylate dimethyl sulfate. Such exemplary cationic surface stabilizers and other useful cationic surface stabilizers are described in J. Cross and E. Singer, Cationic Surfactants: Analytical and Biological Evaluation, Marcel Dekker (1994); P. and D. Rubingh, Ed., Cationic Surfactants: Physical Chemistry, Marcel Dekker (1991); and J. Richmond, Cationic Surfactants: Organic Chemistry, Marcel Dekker (1990).

Most of these surface stabilizers are known pharmaceutical excipients and are described in detail in the Handbook of Pharmaceutical Excipients, published jointly by the American Pharmaceutical Association and The Pharmaceutical Society of Great Britain (The Pharmaceutical Press, 2000), specifically incorporated by reference. The surface stabilizers are commercially available and/or can be prepared by techniques known in the art.

Combinations of more than one surface stabilizer can be used in the invention. Exemplary primary surface stabilizers include, but are not limited to, poloxamers, hydroxypropyl methylcellulose, hydroxypropylcellulose, polyvinylpyrrolidone, random copolymers of vinyl pyrrolidone and vinyl acetate or a combination thereof. Exemplary secondary surface stabilizers include, but are not limited to, sodium lauryl sulfate and dioctylsulfosuccinate.

In exemplary embodiments, the at least one surface stabilizer is a poloxamer. Exemplary poloxamers useful for the invention can have a molecular weight of from about 9,000 to about 20,000. Specific exemplary poloxamers that can be used in the invention include poloxamer 407 and poloxamer 338 or equivalent materials such as corresponding Pluronics.

The concentration of the at least one surface stabilizer can vary from about 0.5% to about 99.999%, from about 5.0% to about 99.9%, from about 1.0% to about 99.0%, or from about 10% to about 99.5%, by weight, based on the total combined dry weight of the active agent and at least one surface stabilizer, not including other excipients. If a combination of two or more surface stabilizers is employed in the composition, the concentration of at least one primary surface stabilizer can vary from about 0.01% to about 99.5%, from about 0.1% to about 95%, or from about 0.5% to about 90%, by weight, based on the total combined dry weight of the active agent not including other excipients.

In some embodiments, the surface stabilizer may be present in an amount of from about 0.1% to about 5%, for example from about 0.1% to about 2.5%, from about 0.1% to about 1%, or from about 0.25% to about 1%. In some embodiments of the invention that are in the form of a suspension, the surface stabilizer may be present in an amount of from about 0.1% to about 5%, for example from about 0.1% to about 2.5%, from about 0.1% to about 1%, or from about 0.25% to about 1%. In some embodiments of the invention that are in the form of a suspension, the surface stabilizer may be present in an amount of about 0.1%, about 0.025%, about 1%, about 2%, or about 2.5%. In other exemplary embodiments, the surface stabilizer may be present in an amount of from about 1% to about 20%, for example from about 10% to about 25%, from about 1% to about 20%, or from about 1% to about 10%. In other exemplary embodiments of a dried form of the composition, the surface stabilizer may be present in an amount of from about 1% to about 20%, for example from about 10% to about 25%, from about 1% to about 20%, or from about 1% to about 10%. In other exemplary embodiments of a dried form of the composition, the surface stabilizer may be present in an amount of about 25%, about 20%, about 10%, about 5%, or about 1%.

Embodiments of the invention can include a ratio of active agent to surface stabilizer in the range of from about 100:1 to about 5:1. In some embodiments, the ratio of active agent to surface stabilizer is from about 200:1 to about 1:1, from about 100:1 to about 10:1, from about 20:1 to about 5:1, or from about 15:1 to about 10:1. In exemplary embodiments, which the ratio of active agent to surface stabilizer is about 100:1, about 50:1, about 25:1, about 10:1, about 12.5:1, about 5:1.

Processes for Preparing the Nanoparticle Compositions

The nanoparticulate compositions of the present invention can be made using, e.g., milling, homogenization or precipitation techniques.

API morphology can be characterized by optical microscopy (e.g., Olympus BX51 microscope with Clemex JS-2000 controller). Differential scanning calorimetry (e.g., Mettler-Toledo DSC 1) and thermogravimetric analysis (e.g., Mettler-Toledo TGA/DSC 1) can be used to measure the thermal characteristics of the material. Particle size measurements can be made throughout by, for example, laser diffraction (e.g. Horiba LA-950V2), by dispersing the material, either in water, when surfactant is present in the test sample or in a dilute solution of poloxamer when no other dispersant was present.

Prototype formulations are processed in glass sample vials on a roller mill (U.S. Stoneware) using a slurry of 0.5 mm diameter yttria-stabilized zirconia ceramic milling media (from, e.g. Tosoh). GLP milling is done in 2 L media bottles of Type 1 borosilicate glass. Preparations of the test article material are done under "best-clean" conditions, under which all contact materials and equipment are sanitized either by application of 70% isopropanol or by autoclaving. All such preparations are performed using aseptic technique in a sanitized laminar flow hood (Airclean 600).

Milling the active agent to obtain a nanoparticulate dispersion involves dispersing particles of the active agent in a liquid dispersion medium in which the active agent is poorly soluble, followed by applying mechanical means in the presence of milling media to reduce the particle size of the active agent to the desired effective average particle size. The dispersion medium can be, e.g., water, ethanol, t-butanol, glycerin, polyethylene glycol (PEG), hexane or glycol.

In embodiments, aqueous nanomilling of the active agent is conducted in the presence of a hydrophilic stabilizer of the surface stabilizer. For example, the active agent particles can be reduced in size in the presence of the at least one surface stabilizer. Alternatively, the active agent particles can be contacted with one or more surface stabilizers after attrition. Other compounds, such as a diluent, can be added to the active agent/surface stabilizer composition either before, during or after the size reduction process. Dispersions can be manufactured continuously or in a batch mode.

In other embodiments, the nanoparticulate composition is prepared by microprecipitation. This is a method of preparing stable dispersions of poorly soluble active agents in the presence of one or more surface stabilizers and one or more colloidal stability enhancing surface active agents free of any trace toxic solvents or solubilized heavy metal impurities. Such a method comprises, e.g., (1) dissolving the active agent in a suitable solvent; (2) adding the formulation from step (1) to a solution comprising at least one surface stabilizer; and (3) precipitating the formulation from step (2) using an appropriate non-solvent or anti-solvent. The method can be followed by removal of any formed salt, if present, by dialysis or diafiltration and concentration of the dispersion by conventional means.

In yet other embodiments, the nanoparticle compositions are prepared by homogenization methods. Such methods include the step of dispersing the active agent particles in a liquid dispersion medium, followed by subjecting the dispersion to homogenization to reduce the particle size of the active agent to the desired effective average particle size. The active agent particles can be reduced in size in the presence of at least one surface stabilizer. Alternatively, the active agent particles can be contacted with one or more surface stabilizers either before or after attrition. Other compounds, such as a diluent, can be added to the active agent/surface stabilizer composition either before, during, or after the size reduction process. Dispersions can be manufactured continuously or in a batch mode.

Compositions according to the invention can be prepared in either the form of a suspension or as a dry powder. For preparation of a suspension, the active agent is reduced in size using one of the previously described techniques. The size reduction may be accomplished using the active agent alone, the active agent dispersed in a solvent, for example water or another solvent as mentioned above, the active agent in combination with the surface stabilizer or a combination of the active agent, solvent and surface stabilizer. Size reduction is continued until the desired particle size of the active agent is achieved. Additional surface stabilizer can be added to achieve the final desired concentration. Furthermore, if desired, the suspension can be diluted with a suitable solvent to reach a desired concentration of active agent. If a solvent is present during size reduction, dilution can be accomplished by adding additional solvent, which may the same or different than the solvent used during size reduction. The term solvent as used herein includes a single solvent or a mixture of solvents. As described above, additional components may be present during the size reduction process or may be added afterward as desired.

In an exemplary embodiment, a suspension is prepared by dissolving the surface active agent, for example a poloxamer such as poloxamer 407 or poloxamer 338, in approximately ⅓ of the final amount of solvent, for example purified water, in a suitable container. The active agent, for example, 1-(3,5-dimethoxyphenyl)-4-[(6-fluoro-2-methoxyquinoxalin-3-yl)aminocarbonyl]piperazine, is suspended in the solution of surface active agent. Milling media is added to the container. The suspension is subjected to size reduction until the desired particle size is achieved. For example, the suspension is milled until the D50 or D90 of the particle-size distribution, measured by, for example, laser diffraction, is below a 1,000 nm. The suspension is then removed from the milling media. The media is rinsed and the suspension diluted with solvent to achieve the desired final concentration of active agent, for example 10%. After preparation, the suspension can be assayed to confirm that the particle size and concentration is at the desired level.

Dry formulations can be obtained by removing solvent from the suspension. Solvent removal can be conducted on either the suspension as obtained immediately after size reduction or after further dilution. Any suitable method of drying may be used that results in a stable formulation. Exemplary methods of drying include spray drying, supercritical drying, drum drying, dielectric drying, natural air drying, Refractance Window™ drying, Infrared Zone Drying™ and freeze drying (lyophilization). In an exemplary method of drying, the suspension is freeze dried by being pre-frozen using liquid nitrogen and lyophilized in bulk on pre-chilled shelves to produce a dry powder.

Stability

Formulations and compositions according to the present invention are stable, and in particular are stable upon storage. In the present context, a stable formulation or composition is a formulation or composition in which the active agent does not degrade or decompose upon storage and in which the particle size distribution does not change significantly. The particle size does not change significantly if, upon storage, the median particle size does not increase to greater than 1,000 nm. In exemplary embodiments, the median particle size does not increase to greater than 900 nm, greater than 800 nm, greater than 700 nm, greater than 600 nm, or greater than 500 nm, upon storage. As used herein, the active agent does not degrade or decompose upon storage if, after storage, at least 95% of the originally present active agent remains. In exemplary embodiments, at least 95%, at least 96%, at least 97%, at least 98%, or at least 99% of the original amount of active agent is present after storage.

Storage conditions for stability testing can be varied and testing may be accomplished under typical storage conditions or under accelerated storage conditions. As used herein, stable under storage conditions or "storage stable" means that the composition is stable when stored at 5° C. for one week. Some embodiments of the invention are storage stable for even longer periods of time, for example after storage at 5° C. for two weeks, for three weeks, or for four weeks. Capsules containing the dried formulation can be stable for even longer periods, for example up to one month, up to two months, up to three months, up to four months, up to five months, up to six two months, or even longer.

Pharmaceutical Compositions and Methods of Treatment

The pharmaceutical compositions of the present invention also include one or more excipients. Excipients include physiologically acceptable carriers, adjuvants or vehicles, collectively referred to as carriers. The compositions can be formulated for oral administration in solid, or liquid form, and the like.

Excipients can include one or more binding agents, filling agents, lubricating agents, suspending agents, sweeteners, flavoring agents, preservatives, buffers, wetting agents, disintegrants, effervescent agents and other excipients. Such excipients are known in the art. Examples of filling agents include lactose monohydrate, lactose anhydrous, microcrystalline cellulose, such as Avicel® PH101 and Avicel® PH102, microcrystalline cellulose and silicified microcrystalline cellulose (ProSolv SMCC®), and various starches; examples of binding agents are various celluloses and cross-linked polyvinylpyrrolidone. Suitable lubricants, including agents that act on the flowability of the powder to be compressed, include colloidal silicon dioxide, such as Aerosil® 200, talc, stearic acid, magnesium stearate, calcium stearate and silica gel. Sweeteners can be any natural or artificial sweetener, such as, for example, sucrose, xylitol, sodium saccharin, cyclamate, aspartame, sucralose, maltitol and acsulfame. Examples of flavoring agents include Magnasweet® (trademark of MAFCO), bubble gum flavor, and fruit flavors, and the like. Examples of preservatives include potassium sorbate, methylparaben, propylparaben, benzoic acid and its salts, other esters of parahydroxybenzoic acid, such as butylparaben; alcohols, such as ethyl or benzyl alcohol. Suitable diluents include pharmaceutically acceptable inert fillers, such as microcrystalline cellulose, lactose, dibasic calcium phosphate, saccharides and/or mixtures of any of the foregoing. Examples of diluents include microcrystalline cellulose, such as Avicel® PH101 and Avicel® PH1 02; lactose, such as lactose monohydrate, lactose anhydrous, and Pharmatose® DCL21; dibasic calcium phosphate, such as Emcompress®; mannitol; starch; sorbitol; sucrose; and glucose. Suitable disintegrants include lightly crosslinked polyvinyl pyrrolidone, corn starch, potato starch, maize starch, and modified starches, croscarmellose sodium, cross-povidone, sodium starch glycolate and mixtures thereof. Examples of effervescent agents are effervescent couples, such as an organic acid and a carbonate or bicarbonate. Suitable organic acids include, e.g., citric, tartaric, malic, fumaric, adipic, succinic and alginic acids and anhydrides and acid salts. Suitable carbonates and bicarbonates include, e.g., sodium carbonate, sodium bicarbonate, potassium carbonate, potassium bicarbonate, magnesium carbonate, sodium glycine carbonate, L-lysine carbonate and arginine carbonate. Alternatively, only the sodium bicarbonate component of the effervescent couple may be present.

The nanoparticulate compositions of the invention can be administered to a subject via any conventional means including orally and parenterally. As used herein, the term "subject" is used to mean an animal, preferably a mammal, including a human or non-human. The terms patient and subject may be used interchangeably.

Solid dosage forms for oral administration include, but are not limited to, capsules, tablets, pills, powders and granules. In such solid dosage forms, the present nanoparticle composition can be admixed with at least one of the following: (a) one or more inert excipients (or carriers), such as sodium citrate or dicalcium phosphate; (b) fillers or extenders, such as starches, lactose, sucrose, glucose, mannitol and silicic acid; (c) binders, such as carboxymethylcellulose, alignates, gelatin, polyvinylpyrrolidone, sucrose and acacia; (d) humectants, such as glycerol; (e) disintegrating agents, such as cross-linked starches, polyvinylpyrrolidone XL, agar-agar, calcium carbonate, potato or tapioca starch, alginic acid, certain complex silicates and sodium carbonate; (f) solution retarders, such as paraffin; (g) absorption accelerators, such as quaternary ammonium compounds; (h) wetting agents, such as cetyl alcohol and glycerol monostearate; (i) adsorbents, such as kaolin and bentonite; and (j) lubricants, such as talc, calcium stearate, magnesium stearate, solid polyethylene glycols, sodium lauryl sulfate or mixtures thereof. For capsules, tablets and pills, the dosage forms may also comprise buffering agents.

Liquid nanoparticulate dosage forms for oral administration include pharmaceutically acceptable emulsions, solutions, suspensions, syrups and elixirs. In addition to the present nanoparticle composition, the liquid dosage forms may include excipients such as inert diluents commonly used in the art, such as water or other solvents, co-solvents, solubilizing agents and emulsifiers. Non-limiting examples of solvents and co-solvents include ethyl alcohol, isopropyl alcohol, ethyl carbonate, ethyl acetate, benzyl alcohol, benzyl benzoate, propyleneglycol, 1,3-butyleneglycol, dimethylformamide, oils, such as cottonseed oil, groundnut oil, corn germ oil, olive oil, castor oil, and sesame oil, glycerol, tetrahydrofurfuryl alcohol and dimethyl isosorbide, polyethyleneglycols, fatty acid esters of sorbitan, or mixtures of these substances, and the like. The composition can also include adjuvants, such as wetting agents, emulsifying and suspending agents, sweetening, flavoring and perfuming agents.

Dosage unit compositions may contain such amounts of such submultiples thereof as may be used to make up the daily dose. Any dosage amount may be present in a pharmaceutical composition for oral delivery. For example, the solid dosage form for oral delivery may include, for example, from about 0.1 mg to about 500 mg active agent, from about 1 mg to about 500 mg active agent, from about 10 mg to about 250 mg active agent, or any other suitable or desired amount. The solution or suspension form for oral and parenteral delivery may include, for example, from about 1% to about 50% active agent, from about 5% to about 30% active agent, from about 10% to about 20% active agent, or any other suitable or desired amount in a solution or suspension. It will be understood, however, that the specific dose level for any particular patient will depend upon a variety of factors: the type and degree of the cellular or physiological response to be achieved; activity of the specific agent or composition employed; the specific agents or composition employed; the age, body weight, general health, sex and diet of the patient; the time of administration, route of administration and rate of excretion of the agent; the duration of the treatment; drugs used in combination or coincidental with the specific agent; and like factors well-known in the medical arts.

The pharmaceutical compositions of the present invention are useful for treating proliferative diseases or diseases that are associated with or triggered by persistent angiogenesis. A proliferative disease is mainly a tumor disease (or cancer) (and/or any metastases). The inventive compositions are particularly useful for treating a tumor which is a breast cancer, lung cancer, gastrointestinal cancer, including esophageal, gastric, small bowel, large bowel and rectal cancer, glioma, sarcoma, such as those involving bone, cartilage, soft tissue, muscle, blood and lymph vessels, ovarian cancer, myeloma, lymphoma, leukemia, female cervical cancer, endometrial cancer, head and neck cancer, mesothelioma, renal cancer, ureter, bladder and urethral cancers, colon cancer, colorectal cancer, liver cancer, pancreatic cancer, prostate cancer, skin cancers and melanoma. Compounds of the invention have particularly shown effectiveness with respect to ovarian, breast including hormone-dependent breast, prostate, liver, lung, kidney, colon, pancreatic, stomach, and endothelial cancers. The pharmaceutical compositions of the present invention can be combined with other chemotherapeutics to treat a tumor or are useful for a treating a tumor that is refractory to treatment with other chemotherapeutics due to multidrug resistance.

The following non-limiting examples are given to illustrate the present invention. It should be understood, however, that the invention is not to be limited to the specific conditions or details described in these examples.

EXAMPLES

Example 1—Classical formulation of 1-(3,5-Dimethoxyphenyl)-4-[(6-fluoro-2-methoxyquinoxalin-3-yl)aminocarbonyl]piperazine 1-(3,5-Dimethoxyphenyl)-4-[(6-fluoro-2-methoxyquinoxalin-3-yl)aminocarbonyl]piperazine has a very poor solubility in water, less than 0.1 m/ml, and its solubility was tested in several co-solvents. In most cases, the initial clear solution showed varying amounts of precipitation at different points in the dilution schedule. Thus, these classical formulations are not useful in clinical use, although they could be used in some limited purpose in pre-clinical studies.

| Formulation | Concentration | Change of formulation |
|---|---|---|
| DMAC/Cremophor EL/DI water (10/10/80 vol %) | <5 mg/ml | n/a |
| DMAC/Tween 80/DI water (10/10/80 vol %) | ~1 mg/ml | n/a |
| 10% Tween 80 in 65% PEG300 | 3.7 mg/ml | n/a |
| 10% DMAC:90% of 35% Solutol ® HS 15 in water | 10 mg/ml | precipitants at bottom after 5 hr |
| 5% DMAC:95% of 50% Solutol ® HS 15 in water | 10 mg/ml | precipitants at bottom after 3 hr |

*DMAC: N,N-Dimethylacetamide

Example 2—Preparation of Nanoformulation 2.1 Characterization of 1-(3,5-Dimethoxyphenyl)-4-[(6-fluoro-2-methoxyquinoxalin-3-yl)aminocarbonyl]piperazine 1-(3,5-Dimethoxyphenyl)-4-[(6-fluoro-2-methoxyquinoxalin-3-yl)aminocarbonyl]piperazine was a freely flowing, off-white powder that was practically insoluble in water. Particles were crystalline and irregularly shaped. FIG. 1 illustrates particles of 1-(3,5-Dimethoxyphenyl)-4-[(6-fluoro-2-methoxyquinoxalin-3-yl)aminocarbonyl]piperazine at 400× Magnification. FIG. 2 illustrates 1-(3,5-Dimethoxyphenyl)-4-[(6-fluoro-2-methoxyquinoxalin-3-yl) aminocarbonyl]piperazine at 400× magnification under polarized light.

Based on chemical structure, the refractive index of 1-(3,5-dimethoxyphenyl)-4-[(6-fluoro-2-methoxyquinoxalin-3-yl)aminocarbonyl]piperazine was predicted to be 1.637. For particle size measurements, the imaginary component of the refractive index, or the i-value (a unitless factor used by the laser diffraction algorithm to account for the absorption of light by the particles) was determined to be 0.1. Unmilled 1-(3,5-Dimethoxyphenyl)-4-[(6-fluoro-2-methoxyquinoxalin-3-yl)aminocarbonyl]piperazine dispersed readily in an aqueous solution of (Aerosol OT). The median particle size (D50) measured at 13 μm.

Thermogravimetric analysis (see FIG. 3) showed a mass loss of 5.8% at an onset temperature of 105° C., consistent with loss of moisture. Mass loss after 220° C. may be attributable to thermal degradation.

Differential scanning calorimetry (see FIG. 4) confirmed the endotherm related to the initial mass loss at 108° C. 1-(3,5-Dimethoxyphenyl)-4-[(6-fluoro-2-methoxyquinoxalin-3-yl)aminocarbonyl]piperazine melted starting at 163° C. and showed no indication of decomposition until 223° C., confirming the gradual mass loss in the TGA analysis.

These data indicated that the material was thermally stable. From these results, no thermal phenomena were determined that might have a detrimental effect on the milling process.

2.2 Evaluation of Particle Size Reduction

The milling aids selected for the size-reduction trials were poloxamer 407, poloxamer 338, sodium lauryl sulfate, and sodium carboxymethylcellulose. Each was tested at both 0.25% and 1%, by weight. Each of these test solutions was used to mill 1-(3,5-dimethoxyphenyl)-4-[(6-fluoro-2- methoxyquinoxalin-3-yl)aminocarbonyl]piperazine (API) at both 12.5% and 25%, by weight. Samples were rolled and tested at intervals, depending on the observed progress of the particle size reduction. The data are shown in Table 1. The poloxamers appeared to perform better at higher concentrations with less API, while sodium lauryl sulfate performed better at lower concentration with more API in short time milling (120 minutes), but with less API in longer time milling (240 minutes and 300 minutes), and sodium carboxymethylcellulose did not prove to be an effective milling aid for API. After 360 minutes of milling, the two most promising candidates were 1% poloxamer 407 with 12.5% API and 1% poloxamer 338 with 12.5% API. All others showed attenuation in efficacy, no appreciable efficacy, or an increase in particle size, either due to agglomeration caused by over-milling or ripening. (As understood in the art, ripening occurs when small crystals or particles dissolve and redeposit onto larger crystals or particles.) The two poloxamer preparations were maintained at both ambient conditions and at 5° C. as an informal assessment of their particle-size stability. The measurements remained virtually unchanged over four weeks as shown in Table 2.

TABLE 1

Initial dispersant selection data

| Dispersant | | API | Median Particle Size (D50) at: | | | | |
|---|---|---|---|---|---|---|---|
| | | | 0 min | 120 min | 240 min | 300 min | 360 min |
| Poloxamer 407 | 0.25% | 12.5% | 13 | 1.9 μm | 3.8 μm | 3.1 μm | N/A |
| | | 25% | | 5.3 μm | 4.2 μm | 6.0 μm | N/A |
| | 1% | 12.5% | | 0.4 μm | 1.2 μm | 0.2 μm | 0.1 μm |
| | | 25% | | 1.3 μm | 2.5 μm | 2.1 μm | N/A |
| Poloxamer 338 | 0.25% | 12.5% | 13 | 2.4 μm | 0.5 μm | 1.3 μm | N/A |
| | | 25% | | 8.4 μm | 5.9 μm | 5.9 μm | N/A |
| | 1% | 12.5% | | 0.2 μm | 0.2 μm | 0.2 μm | 0.2 μm |
| | | 25% | | 6.3 μm | 3.5 μm | 4.7 μm | N/A |
| Sodium Lauryl Sulfate | 0.25% | 12.5% | 13 | 1.4 μm | 0.2 μm | 0.9 μm | N/A |
| | | 25% | | 0.3 μm | 1.8 μm | 2.4 μm | N/A |
| | 1% | 12.5% | | 3.0 μm | 2.7 μm | 1.2 μm | N/A |
| | | 25% | | 3.5 μm | 3.3 μm | 2.8 μm | N/A |
| Sodium Carboxymethylcellulose | 0.25% | 12.5% | 13 | 15 μm | N/A | N/A | N/A |
| | | 25% | | 14 μm | N/A | N/A | N/A |
| | 1% | 12.5% | | 12 μm | N/A | N/A | N/A |
| | | 25% | | 16 μm | N/A | N/A | N/A |

TABLE 2

Particle-size stability of 12.5% API trial preps

| Prep | Condition | Median Particle Size (D50) at: | | | | |
|---|---|---|---|---|---|---|
| | | Initial | 1 Week | 2 Weeks | 3 Weeks | 4 Weeks |
| 1% Poloxamer 407 | Ambient | 0.2 μm | 0.2 μm | 0.1 μm | 0.1 μm | 0.1 μm |
| | 5° C. | | 0.2 μm | 0.2 μm | 0.1 μm | 0.1 μm |
| 1% Poloxamer 338 | Ambient | 0.2 μm | 0.2 μm | 0.2 μm | 0.2 μm | 0.2 μm |
| | 5° C. | | 0.2 μm | 0.2 μm | 0.2 μm | 0.2 μm |

The suspension of 25% API in 0.25% sodium lauryl sulfate (SLS) showed initial promise under the test conditions, but resulted in eventual particle-size increase (e.g., by ripening) during milling. In order to rule out the possibility of particle fusion by overmilling, a second preparation was made by milling only a total of 120 minutes, and then monitored for particle size. After one week, the preparation showed evidence of ripening as shown in Table 3:

TABLE 3

Particle-size stability of SLS Repreparation

| Prep | Condition | Median Particle Size, in microns | |
|---|---|---|---|
| | | Initial | 1 Week |
| 0.25% SLS with 25% API | Ambient | 0.3 μm | 0.8 μm |
| | 5° C. | | 0.5 μm |

2.3 Prototype Formulation Manufacturing

Given the comparable performance of both poloxamers as milling agents, poloxamer 407 was chosen for the prototype formulation instead of poloxamer 338 due to a more favorable toxicity profile. In order to facilitate milling the quantities of test article required for study, a test batch was made at 30% API with a proportional increase in poloxamer 407 to 2.4%. The median particle-size was successfully reduced to the submicron range with additional milling time:

TABLE 4

Particle-size reduction of concentrated suspension

| Milling Time (min) | Median Particle Size (D50) |
|---|---|
| 300 | 1.2 μm |
| 360 | 0.8 μm |

TABLE 4-continued

Particle-size reduction of concentrated suspension

| Milling Time (min) | Median Particle Size (D50) |
|---|---|
| 480 | 0.7 μm |
| 540 | 0.5 μm |
| 600 | 0.1 μm |

The concentrated suspension was diluted with deionized water to the target concentration of 10% API and that dilution was monitored for stability at ambient conditions. The particle size distribution was stable for four weeks:

TABLE 5

Particle-size stability of diluted concentrate

| Time | Median |
|---|---|
| Initial | 0.1 μm |
| 1 Week | 0.2 μm |
| 2 Weeks | 0.2 μm |
| 4 Weeks | 0.2 μm |

From these data, the prototype formulation for the 1-(3,5-dimethoxyphenyl)-4-[(6-fluoro-2-methoxyquinoxalin-3-yl)aminocarbonyl]piperazine nanosuspension was prepared, as follows:

Dissolve poloxamer 407 in approximately ⅓ of the purified water in a suitable milling container.

Suspend 1-(3,5-dimethoxyphenyl)-4-[(6-fluoro-2-methoxyquinoxalin-3-yl)aminocarbonyl]piperazine in the poloxamer 407 solution.

1. Add sufficient milling media to fill the container approximately halfway.
2. Roll container on roller mill until the D90 of the particle-size distribution, measured by laser diffraction, is below a micron (refractive index 1.637/i-value 0.1).
3. Extract suspension from milling media.
4. Rinse the media with a portion of the remaining water, transferring the rinsate to the extracted suspension.
5. Assay the suspension.
6. Based upon the measured assay value, dilute the final suspension with the remaining water to a concentration of 10%.
7. Assay the suspension for confirmation.

More specifically, API was suspended at 300 mg/g in a 2.4% w/w solution of poloxamer 407 in sterile water. 0.5 mm YTZ ceramic milling media (yttria-stabilized zirconia medium from Nikkato Corporation) was added and the suspension was milled using a roller mill until the particle size (D90), measured by laser diffraction, was not more than 2 micron and the median particle size (D50) was not more than 500 nm. After milling, the suspension was diluted with sterile water to 100 mg/g API.

TABLE 6

Prototype Nanosuspension Formulation

| Component | % w/w |
|---|---|
| Water, Purified, USP | 89.2% |
| Poloxamer 407, NF | 0.8% |
| 1-(3,5-dimethoxyphenyl)-4-[(6-fluoro-2-methoxyquinoxalin-3-yl)aminocarbonyl]piperazine (API) | 10.0% |

2.4 Prototype Manufacturing for GLP Studies

In detail, 472.9 grams of API was milled in three separate batches at 30% concentration each. The milling media from each batch was extracted with part of the remaining water and all the extracts were combined. The assay value of the in-process suspension measured 201 mg/g (20.1%). Based on this value, the suspension was diluted to a final concentration of 10% drug substance using sterile water for injection and an additional poloxamer 407 to bring the total poloxamer concentration to 2.05%. The net yield of the final suspension was 4,528 grams; at an assay value of 103 mg/g, the total API yield was 466.4 grams, or 98.6% of the original amount of API.

Example 3—Drug Product

The nanosuspension was pre-frozen using liquid nitrogen and lyophilized in bulk on pre-chilled shelves to produce a dry powder. The dry powder was manually weighed into a weighed funnel and then placed into hydroxypropyl methyl cellulose capsule shells (size 0) and packaged in quantities of 10 capsules per 30 ml high density polyethylene plastic bottle with a 5 g desiccant pack. Capsules containing 60 mg of active pharmaceutical ingredient were prepared. API lyophilized powder, 60 mg fill per capsule, has the following composition (Table 7) and batch formula (Table 8).

TABLE 7

Composition

| Component | Amount per capsule |
|---|---|
| API | 50 mg |
| Poloxamer 407 | 10.25 mg |

TABLE 8

Batch Formula

| Step | Component | Concentration |
|---|---|---|
| Milling | API | 30.00% (w/w) |
| | Poloxamer 407 | 2.40% (w/w) |
| | Water | 67.60% (w/w) |
| Dilution and | API | 10.00% (w/w) |
| Poloxamer | Poloxamer 407 | 2.05% (w/w) |
| Addition | Water | 87.95% (w/w) |
| Lyophilized | API | 82.99% (w/w) |
| powder | Poloxamer 407 | 17.01% (w/w) |

Example 4—Stability of Drug Product 60 mg of Lyophilized powder API in size 0 hydroxypropyl methyl cellulose capsule (to deliver 50 mg of API) stored in amber bottle with desiccant packet and induction sealed. The capsules were stored at 5° C. or 25° C./60% relative humidity (RH) and the API and water content in capsule, particle size of API were analyzed. The data is shown in Table 9.

TABLE 9

Stability of drug product.

| Storage condition | Test Parameter | Initial | 1 Month | 2 Month | 3 Month | 6 Month |
|---|---|---|---|---|---|---|
| 5° C. | PSD | (D10) 0.08 μm<br>(D50) 0.17 μm<br>(D90) 1.6 μm | (D10) 0.08 μm<br>(D50) 0.19 μm<br>(D90) 2.3 μm | (D10) 0.08 μm<br>(D50) 0.20 μm<br>(D90) 2.1 μm | (D10) 0.08 μm<br>(D50) 0.19 μm<br>(D90) 2.3 μm | (D10) 0.08 μm<br>(D50) 0.18 μm<br>(D90) 1.7 μm |
| | Water Content | 0.1% | <0.1% | <0.1% | <0.1% | <0.1% |
| | Assay | 98.0% | 98.9% | 98.5% | 100.9% | 97.8% |
| 25° C./60% RH | PSD | (D10) 0.08 μm<br>(D50) 0.17 μm<br>(D90) 1.6 μm | (D10) 0.09 μm<br>(D50) 0.24 μm<br>(D90) 2.8 μm | (D10) 0.17 μm<br>(D50) 1.5 μm<br>(D90) 6.8 μm | (D10) 0.17 μm<br>(D50) 1.5 μm<br>(D90) 6.7 μm | (D10) 0.18 μm<br>(D50) 1.6 μm<br>(D90) 7.1 μm |
| | Water Content | 0.1% | <0.1% | <0.1% | <0.1% | <0.1% |
| | Assay | 98.0% | 98.8% | 98.1% | 97.0% | 95.4% |

PSD = particle size distribution

As shown in Table 9, storage of drug product at 25° C./60% RH for 6 months resulted in the increase of particle size and decrease of API content. Storage at 5° C. showed no increase in particle size and no decrease in API content for 6 months. Given the stability data in Table 9, 5° C. was chosen for the storage of drug product.

CONCLUSIONS FROM EXAMPLES

Roller milling was found to be a simple, effective means by which to reduce the particle size of API. When processed with poloxamers as milling aids, even at concentrations as high as 30% API, no fusing, ripening, discoloration or other detrimental physical phenomena were observed. Sodium lauryl sulfate, while it was shown to reduce the particle size at very low concentrations, caused ripening, possibly due to a cosolvency effect with the API. The use of a concentrated suspension with an in-process assay allowed for multiple batches to be processed, combined and diluted to the desired concentration for the toxicity study. This made possible the processing of over 470 grams of API with nearly 99% recovery using laboratory-scale apparatus.

The embodiments illustrated and discussed in this specification are intended only to teach those skilled in the art the best way known to the inventors to make and use the invention. Nothing in this specification should be considered as limiting the scope of the present invention. All examples presented are representative and non-limiting. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A stable composition comprising nanoparticles; wherein the nanoparticles comprise:
   (a) the compound of formula (1),

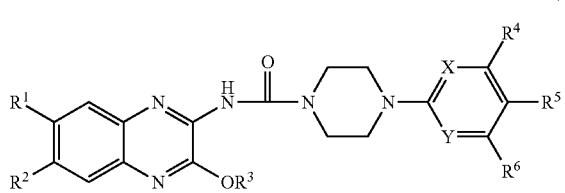

(1)

or pharmaceutically acceptable salts thereof, wherein
   X and Y are independently N or C—$R^7$;
      $R^1$ is hydrogen, $C_1$-$C_3$ alkoxy, $C_1$-$C_3$ alkyl or halogen and $R^2$ is F; or
      $R^1$ is F and $R^2$ is hydrogen, $C_1$-$C_3$ alkoxy, $C_1$-$C_3$ alkyl or halogen;
   $R^3$ is $C_1$-$C_3$ alkyl; and
   $R^4$, $R^5$, $R^6$ and $R^7$ are independently H, $C_1$-$C_6$ alkoxy, $C_1$-$C_6$ alkyl, $C_1$-$C_6$ haloalkyl, $C_1$-$C_6$ alkylcarbonyl, cyano, nitro or halogen; and
   (b) at least one surface stabilizer comprising a poloxamer selected from poloxamer 407 or poloxamer 338, wherein the nanoparticles have an effective median particle size (D50) of less than about 1,000 nm.

2. The composition of claim 1, wherein the compound of formula 1 is 1-(3,5-dimethoxyphenyl)-4-[(6-fluoro-2-methoxyquinoxalin-3-yl)aminocarbonyl]piperazine.

3. The composition of claim 1, in the form of a liquid suspension or a dry powder.

4. The composition of claim 1, wherein the composition is stable after storage for at least four weeks.

5. The composition of claim 1, wherein the effective median particle size is of less than about 500 nm.

6. The composition of claim 1, wherein the ratio (wt/wt) of the compound of formula (1) to surface stabilizer is from about 100:1 to about 5:1.

7. A method of making a storage stable composition comprising preparing a mixture of
   (a) particles of a compound of formula (1),

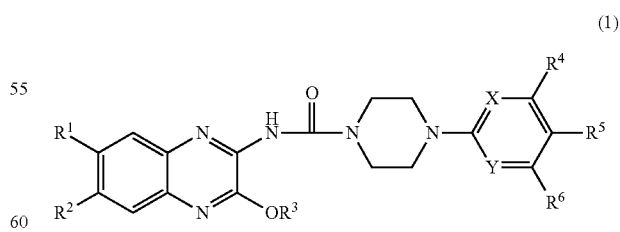

(1)

or pharmaceutically acceptable salts thereof,
wherein
   X and Y are independently N or C—$R^7$;
   for the combination of variables $R^1$ and $R^2$:
      $R^1$ is hydrogen, $C_1$-$C_3$ alkoxy, $C_1$-$C_3$ alkyl or halogen and $R^2$ is F; or $R^1$ is F and $R^2$ is hydrogen, $C_1$-$C_3$ alkoxy, $C_1$-$C_3$ alkyl or halogen;

$R^3$ is $C_1$-$C_3$ alkyl; and $R^4$, $R^5$, $R^6$ and $R^7$ are independently H, $C_1$-$C_6$ alkoxy, $C_1$-$C_6$ alkyl, $C_1$-$C_6$ haloalkyl, $C_1$-$C_6$ alkylcarbonyl, cyano, nitro or halogen; and (b) at least one surface stabilizer comprising a poloxamer selected from poloxamer 407 or poloxamer 338, and reducing the size of the particles of a compound of the formula (1) under conditions sufficient to provide a nanoparticulate suspension having an effective median particle size of less than about 1,000 nm, thereby producing a stable composition.

8. The method of claim 7, further comprising drying the nanoparticulate suspension, by lyophilization, to form a powder.

9. The method of claim 7, wherein the mixture comprises from about 5% to about 50% of the compound of formula 1 and from about 0.1% to about 5% of the surface stabilizer.

10. The method of claim 7, wherein the powder comprises from about 75% to about 90% of the compound formula 1 and from about 10% to about 25% of the surface stabilizer.

11. The method of claim 7, wherein the ratio of the compound of formula (1) to surface stabilizer is from about 100:1 to about 5:1.

12. The method of claim 7, wherein the reducing comprises grinding, homogenizing or precipitating.

13. The method of claim 12, wherein the reducing comprises grinding from about 360 to about 600 minutes.

14. The method of claim 7, wherein the compound of formula 1 is 1-(3,5-dimethoxyphenyl)-4-[(6-fluoro-2-methoxyquinoxalin-3-yl)aminocarbonyl]piperazine.

15. The method of claim 7, further comprising adding water to the mixture after reducing the size of the particles.

16. A pharmaceutical composition comprising the composition of claim 1 and at least one pharmaceutically acceptable excipient.

17. The pharmaceutical composition of claim 16, wherein the at least one pharmaceutically acceptable excipient comprises water or hydroxypropyl methylcellulose.

18. The pharmaceutical composition of claim 16, wherein the composition is an oral dosage form or a parenteral dosage form.

19. The pharmaceutical composition of claim 16, comprising about 0.01 to about 250 mg of the compound of formula (1).

\* \* \* \* \*